US008957663B2

(12) United States Patent
Morimoto et al.

(10) Patent No.: US 8,957,663 B2
(45) Date of Patent: Feb. 17, 2015

(54) CELLULAR POTENTIAL MEASUREMENT CONTAINER AND PRODUCTION METHOD THEREFOR

(75) Inventors: Shinji Morimoto, Osaka (JP); Yui Hagiwara, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 13/511,746

(22) PCT Filed: Nov. 22, 2010

(86) PCT No.: PCT/JP2010/070839
§ 371 (c)(1),
(2), (4) Date: May 24, 2012

(87) PCT Pub. No.: WO2011/068057
PCT Pub. Date: Jun. 9, 2011

(65) Prior Publication Data
US 2012/0286762 A1    Nov. 15, 2012

(30) Foreign Application Priority Data

Dec. 1, 2009  (JP) .................................. 2009-273522

(51) Int. Cl.
*G01R 31/02*    (2006.01)
*C12M 1/34*    (2006.01)
*C12M 1/32*    (2006.01)

(52) U.S. Cl.
CPC ............... *C12M 41/46* (2013.01); *C12M 23/12* (2013.01)
USPC ............... 324/72; 324/76; 324/157; 324/447; 324/450

(58) Field of Classification Search
CPC ....................................................... H01L 24/11
USPC .............................. 324/72, 76, 157, 447, 450
See application file for complete search history.

(56) References Cited

U.S. PATENT DOCUMENTS 4,236,977 A * 12/1980 Azzerri et al. ................ 205/140
5,198,092 A *  3/1993 Kiesele et al. ............... 204/402
(Continued)

FOREIGN PATENT DOCUMENTS

JP     2004140014 A    5/2004
JP     2007534927 A   11/2007
(Continued)

OTHER PUBLICATIONS

Catalog of QT-Screen, automated measurement system for high-throughout QT prolongation, made by Multi Channel Systems, issued by Bio Research Center Co., Ltd., www.brck.co.jp/MCS/qtscreencataloguejp1.pdf, with partial translation, 5 pages, Available online on :Aug. 12, 2006.
(Continued)

*Primary Examiner* — Tung X Nguyen
*Assistant Examiner* — Giovanni Astacio-Oquendo
(74) *Attorney, Agent, or Firm* — The Webb Law Firm

(57) ABSTRACT

A container for measuring cellular electric potential after being mounted on an electric potential measuring device is provided comprising a container and an electrode substrate, the electrode substrate being attached to a lower end of the container so as to form a plurality of wells, wherein the container comprises a plurality of cylindrical portions whose upper and lower ends are open, the electrode substrate comprises a substrate and a plurality of measurement electrodes and a plurality of reference electrodes disposed on one surface of the substrate, the measurement electrodes and the reference electrodes at least comprise metal-plated copper wiring, a pair of a measurement electrode and a reference electrode are disposed on a bottom of each well, and the measurement electrodes and the reference electrodes are formed by a pre-plating method.

2 Claims, 2 Drawing Sheets

(56) References Cited

U.S. PATENT DOCUMENTS

| | | | |
|---|---|---|---|
| 5,676,812 A * | 10/1997 | Kadokura | 205/50 |
| 6,682,649 B1 * | 1/2004 | Petersen et al. | 205/777.5 |
| 6,977,722 B2 * | 12/2005 | Wohlstadter et al. | 356/246 |
| 6,984,297 B2 * | 1/2006 | Nisch et al. | 204/403.01 |
| 7,611,850 B2 | 11/2009 | Maher et al. | |
| 7,615,356 B2 | 11/2009 | Maher et al. | |
| 7,678,249 B2 | 3/2010 | Ozaki et al. | |
| 7,923,537 B2 | 4/2011 | Maher et al. | |
| 8,318,477 B2 * | 11/2012 | Nakatani et al. | 435/288.3 |
| 2003/0113833 A1 * | 6/2003 | Oka et al. | 435/29 |
| 2003/0145949 A1 * | 8/2003 | Tanaka et al. | 156/330 |
| 2004/0262730 A1 * | 12/2004 | Yamaji et al. | 257/678 |
| 2005/0064703 A1 * | 3/2005 | Kondo et al. | 438/633 |
| 2007/0062725 A1 * | 3/2007 | Wu et al. | 174/260 |
| 2009/0250354 A1 * | 10/2009 | Takamatsu et al. | 205/215 |
| 2010/0133122 A1 | 6/2010 | Ozaki et al. | |
| 2010/0304423 A1 * | 12/2010 | Asai et al. | 435/29 |

FOREIGN PATENT DOCUMENTS

| | | |
|---|---|---|
| WO | 2005001018 A1 | 1/2005 |
| WO | 2009038079 A1 | 3/2009 |

OTHER PUBLICATIONS

Catalog, "QT-Screen, Automated Cardiac Electrophysiology for Drug Profiling and Safety Screening" by Multi-Channel Systems, 6 pages, http://www.lohres.de/products/05_qt-screen.htm, Available Online on: Mar. 20, 2008.

* cited by examiner

CELLULAR POTENTIAL MEASUREMENT CONTAINER AND PRODUCTION METHOD THEREFOR

TECHNICAL FIELD

The present invention relates to a cellular electric potential measuring container for measuring cellular electric potential after being mounted on an electric potential measuring device, and a production method therefor.

BACKGROUND ART

In current new drug development, it is necessary to discover the toxicity caused by a drug at an early stage. One known example of this toxicity is drug-induced (acquired) QT prolongation syndrome, which is a disease that causes severe arrhythmia in a patient.

Drug-induced QT prolongation syndrome is a serious disease with which QT interval prolongation appears on an electrocardiogram after drug administration, and ventricular fibrillation often occurs after TdP (Torsades de pointes: non-sustained polymorphic ventricular tachycartha), resulting in syncope or sudden death. In fact, out of the 25 drugs whose sales were stopped in the US market after 1980, five drugs have been determined as causing drug-induced QT prolongation syndrome.

In this regard, to discover toxicity that is caused by a drug, non-patent literature 1 discloses a measurement method in which the effect of a drug on the activity of an ion channel is analyzed based on the change in the electric potential of a cell in a drug-administered culture solution. This measurement method is carried out once a cellular electric potential measuring container is mounted on an electric potential measuring device. This cellular electric potential measuring container includes a plurality of wells for accommodating a culture solution and cells, and a measurement electrode and a reference electrode are disposed on the bottom of each well.

However, with the foregoing measurement system, cells to be measured may weaken or die, sometimes making it impossible to precisely measure cellular electric potential.

PRIOR ART DOCUMENTS

Non-Patent Documents

Non-Patent Document 1: URL: http://www.brck.co.jp/MCS/qtscreencataloguejp1.pdf

SUMMARY OF INVENTION

Problems to be Solved by the Invention

An object of the present invention is to provide a cellular electric potential measuring container with which an accurate measurement result can be obtained without weakening or killing the cells to be measured in cellular electric potential measurement using a cellular electric potential measuring container.

Means for Solving the Problems

Having conducted diligent research to achieve the above-described object, the inventors found a method that suppresses elution of copper, which is highly cytotoxic, and arrived at the present invention.

The present invention provides a container for measuring cellular electric potential after being mounted on an electric potential measuring device, comprising a container and an electrode substrate, the electrode substrate being attached to a lower end of the container so as to form a plurality of wells, wherein the container comprises a plurality of cylindrical portions whose upper and lower ends are open, the electrode substrate comprises a substrate and a plurality of measurement electrodes and a plurality of reference electrodes disposed on one surface of the substrate, the measurement electrodes and the reference electrodes at least comprise metal-plated copper wiring, a pair of a measurement electrode and a reference electrode are disposed on a bottom of each well, and the measurement electrodes and the reference electrodes are formed by a pre-plating method.

The present invention also provides a method for producing a container for measuring cellular electric potential after being mounted on an electric potential measuring device, wherein the container comprises a container and an electrode substrate, and the electrode substrate is attached to a lower end of the container so as to form a plurality of wells, the container comprises a plurality of cylindrical portions whose upper and lower ends are open, the electrode substrate comprises a substrate and a plurality of measurement electrodes and a plurality of reference electrodes disposed on one surface of the substrate, the measurement electrodes and the reference electrodes comprise at least copper, a pair of a measurement electrode and a reference electrode are disposed on a bottom of each well, and the measurement electrodes and the reference electrodes are formed by a pre-plating method.

The cellular electric potential measuring container of the present invention is a disposable component that is used in a system for measuring a change of cellular electric potential that occurs in response to a plurality of new drug candidate compounds in wells. The cellular electric potential measuring container of the present invention is used after being mounted on a dedicated electric potential measuring device (not shown in figures). The configuration thereof includes a plurality of wells. The wells are formed by attaching an electrode substrate to the lower end of a container. That is, the container serves as the side wall of the wells, and the electrode substrate serves as the bottom of the wells. The formed wells are fluid tight such that a fluid used in a measurement (usually a culture solution) can be accommodated. Both a measurement electrode and a reference electrode are disposed on the bottom of each well. Accordingly, the cellular electric potential can be measured in each well. The term "cell" as used herein should be understood to encompass not only a single cell but also cell mass (spheroid) formed by aggregation of a plurality of cells.

The cellular electric potential measuring container of the present invention is disposable as stated above. Therefore, to attain an inexpensive product, it is desirable that at least the container is entirely made from resin. The resin is not particularly limited in the present invention as long as the resin can be molded into the container and is electrically insulating. Specific examples of the resin include polypropylene, polystyrene, polyester, polycarbonate, and the like. In particular, from the viewpoint of low material cost, high transparency, and good appearance, the resin is preferably polystyrene. A method for producing the container is not necessarily limited as long as the container is readily produced, but given the complex structure of the container, it is usually desirable to produce the container by injection molding.

The upper and lower ends of the cylindrical portions are open. The upper end is open to accommodate a cell and a culture solution when carrying out a measurement, and the lower end is open to allow the electrode substrate, which will be described later, to serve as a bottom. The shape of the cylindrical portions is not particularly limited in the present invention, but it is desirably cylindrical from the viewpoint of easy production.

Meanwhile, the electrode substrate includes a substrate, and a plurality of measurement electrodes and a plurality of reference electrodes are disposed on one surface of the substrate.

The substrate is composed of a so-called electrically insulating material. Examples of the material include polypropylene, polystyrene, polyester, fluororesin, polycarbonate, acrylic resin, paper phenol, paper epoxy, glass composites such as glass epoxy, alumina, and the like. From the viewpoint of ease of constructing the measurement electrodes and the reference electrodes, high mechanical strength, and low cost, in general, glass epoxy is often selected. However, the present invention is not limited by these materials for the substrate.

The measurement electrode is an electrode that comes into contact with a cell and measures the ion channel activity of the cell as electric potential, and the reference electrode is an electrode that comes into contact with a fluid used in a measurement (usually a culture solution) and measures electric potential that is regarded as so-called reference electric potential. The measurement electrode and the reference electrode are disposed in places such that one measurement electrode and one reference electrode are present on the bottom of each well when the electrode substrate is attached to the container and wells are thus formed. As a matter of course, the measurement electrode and the reference electrode on the bottom of each well are not electrically connected. Examples of materials used for plating the measurement electrode and the reference electrode include gold, silver, carbon, platinum, ruthenium oxide, palladium, and the like. These materials are used for plating copper wiring formed on the substrate.

In the present invention, the measurement electrode and the reference electrode are formed by a so-called pre-plating method. The pre-plating method refers to an electrode production method in which specific thermosetting resin paste (solder resist) is printed on a substrate having copper wiring that has been metal-plated in advance, and the thermosetting resin is cured to form protective film. Accordingly, the amount of copper, eluted from the aforementioned plurality of measurement electrodes and plurality of reference electrodes to the fluid accommodated in the wells is kept small. Here, the amount of copper eluted refers to the amount of copper per unit volume of culture medium increased after one electrode substrate is immersed in the culture medium during a specific period of time. More specifically:

(A) If the amount of copper eluted refers to the amount of copper per unit volume of culture medium increased at 24 hours after accommodation in a well, the amount is 0.2 mg/L or less, preferably 0.1 mg/L or less, and most preferably 0.05 mg/L or less.

(B) If the amount of copper eluted refers to the amount of copper per unit volume of culture medium increased at 48 hours after accommodation in a well, the amount is 0.4 mg/L or less, preferably 0.2 mg/L or less, and most preferably 0.1 mg/L or less.

(C) If the amount of copper eluted refers to the amount of copper per unit volume of culture medium increased at 168 hours after accommodation in a well, the amount is 0.8 mg/L or less, preferably 0.4 mg/L or less, and most preferably 0.2 mg/L or less.

Conventional techniques can be used to measure the copper concentration, and examples include measurement with an ICP emission spectrometer, a visible-ultraviolet spectrophotometer, an atomic absorption spectrophotometer, an ion chromatograph, an X-ray fluorescence analyzer, or the like. The fluid accommodated in wells is not particularly limited, and a culture medium that is usually used in the measurement of cellular electric potential, in which the cellular electric potential measuring container of the present invention or the like is employed, may be used. Even if some copper is contained in the culture medium, that will not be a problem because the aforementioned amount of copper eluted refers to the amount of copper increased (the amount of change). However, since copper influences the measurement of cellular electric potential as stated above, it is desirable to use a fluid that does not contain copper as the fluid used for the measurement of cellular electric potential.

The pre-plating method itself is a technique known in the art of substrate forming. However, it has not been known heretofore that copper is eluted into a fluid accommodated in wells of cellular electric potential measuring containers such as the present invention. Furthermore, even a person skilled in the art could not predict that eluted copper weakens or kills the cells to be measured and, therefore, adversely affects the measurement of cellular electric potential.

Attachment of the container to the electrode substrate is not particularly limited in the present invention. For example, as in conventional cellular electric potential measuring containers, attachment may be performed using a double-sided tape or an adhesive.

With the cellular electric potential measuring container of the present invention, copper is not eluted from either a measurement electrode or a reference electrode to a fluid accommodated in a well, and thus an accurate measurement result can be obtained.

MODE FOR CARRYING OUT THE INVENTION

Hereinbelow, embodiments of the present invention will be described using the figures, but the present invention is not construed as being limited to the embodiments described later.

EXAMPLES

Example 1

Figure 1:
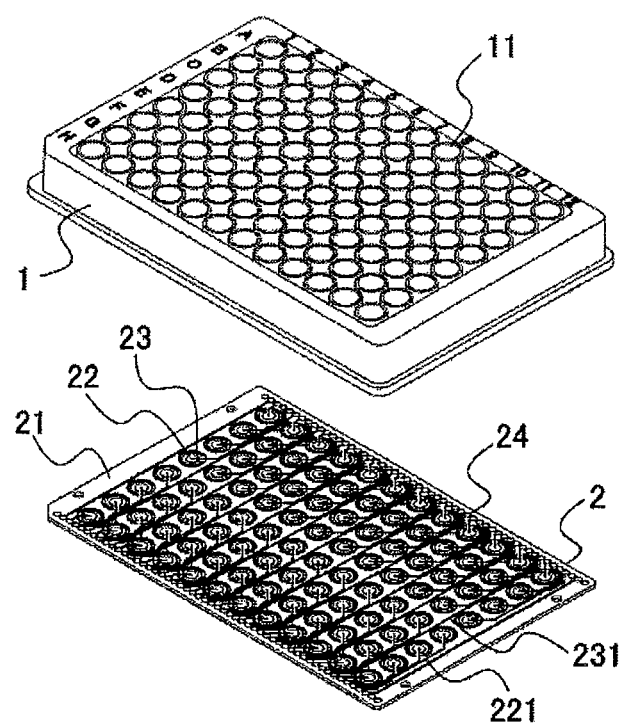
FIG. 1 is an exploded perspective view of the cellular electric potential measuring container of the present invention.

FIG. 1 is an exploded perspective view of the cellular electric potential measuring container of the present invention. The cellular electric potential measuring container of the present invention is primarily composed of a container 1 and an electrode substrate 2. The container 1, which is made from resin, includes a plurality of cylindrical portions 11 having a cylindrical shape whose upper and lower ends are open. The structure of the inner cavity of each cylindrical portion 11 will be described later. Each cylindrical portion 11 constitutes the side wall of a well.

Meanwhile, the electrode substrate 2 forms the bottom of the wells. The electrode substrate 2 includes a substrate 21 composed of an electrically insulating material, and a plurality of measurement electrodes 22 and reference electrodes 23 are disposed on the substrate 21. The measurement electrodes 22 and the reference electrodes 23 contain at least copper. The measurement electrodes 22 and the reference electrodes 23 were produced by a pre-plating method. A measurement electrode 22 of the electrode substrate 2 in FIG. 1 is disposed substantially at the center of a reference electrode 23 that has a C shape. All of the measurement electrodes 22 and reference electrodes 23 are lead by lead wires 221 of the measurement electrodes and lead wires 231 of the reference electrodes that are independent of each other to connectors 24 arranged in-line along one side of the electrode substrate. A reason that the reference electrodes 23 are C-shaped is to secure space for disposing the lead wires 221 of the measurement electrodes to lead the measurement electrodes 22 to the connectors 24. Although not shown, the connectors 24 are also disposed on the opposite surface of the electrode substrate 2 (the surface on which no measurement electrodes 22 or reference electrodes 23 are disposed). When the cellular electric potential measuring container of the present invention is mounted on a dedicated electric potential measuring device (not shown), the connectors 24 on the opposite surface of the electrode substrate 2 are electrically connected to the dedicated electric potential measuring device, thus enabling cellular electric potential to be measured.

Comparative Example 1

The same procedure as in Example 1 was used except that a post-plating method was performed in place of a pre-plating method unlike in the production of the cellular electric potential measuring container of Example 1 above.

Figure 2:
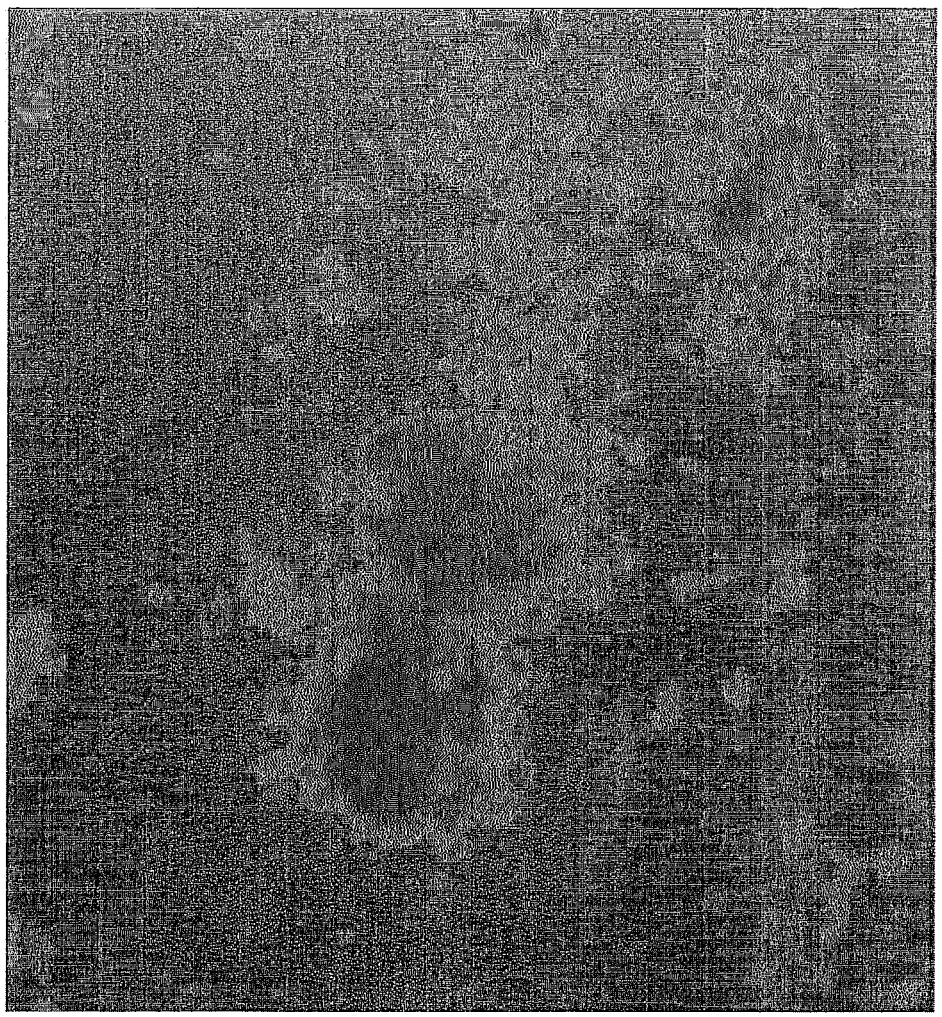
FIG. 2 is an image showing cardiac muscle cells 3 days after the measurement of cellular electric potential using the cellular electric potential measuring container of Comparative Example 1.

FIG. 2 is an image showing cardiac muscle cells (held by Reprocell Inc.) 3 days after starting culturing using the cellular electric potential measuring container of Comparative Example 1. As a fluid used in measurement, a primate ES cell culture medium (Reprocell Inc.) was used. The cardiac muscle cells used were derived from cynomolgus monkey ES cells and were a mass of a large number of cells. The mass of cardiac muscle cells of the comparative example showed weakened pulses as time passed, and cells were destroyed and died within 3 days. Also, the culture medium for the primate ES cells in Comparative Example 1 was discolored. In contrast, the cardiac muscle cells in the cellular electric potential measuring container of Example 1 did not show weakened cellular pulses even after 4 days after measurement, and it was thus confirmed that the cells were alive.

Table 1 shows results of measuring copper concentrations (mg/L) with an ICP emission spectrometer (Shimadzu Corporation: ICPS-8000) after immersing two electrode substrates having different production lots that were used for the cellular electric potential measuring containers of Example 1 (Example 1-1 and Example 1-2) and two electrode substrates having different production lots that were used for the cellular electric potential measuring containers of Comparative Example 1 (Comparative Example 1-1 and Comparative Example 1-2) in 100 mL of an RPMI1640 culture medium, and sampling 10 mL of the medium every time a specific period of time had passed.

TABLE 1

|  | At the beginning | After 24 hours | After 48 hours | After 168 hours |
|---|---|---|---|---|
| Example 1-1 | 0.00 | 0.00 | 0.00 | 0.00 |
| Example 1-2 | 0.00 | 0.00 | 0.00 | 0.00 |
| Comparative example 1-1 | 0.00 | 0.40 | 0.33 | 0.86 |
| Comparative example 1-2 | 0.00 | 10.80 | 38.00 | 97.40 |

Unit: mg/L

It is clear that absolutely no copper was eluted into the RPMI1640 culture medium in the example, whereas copper was eluted into the RPMI1640 culture medium in the comparative example.

A method for measuring cellular electric potential using the cellular electric potential measuring container of the present invention can be performed in a manner comparable to a method that uses a conventional cellular electric potential measuring container.

The present invention enables an accurate measurement of cellular electric potential without weakening or killing the cell to be measured, and therefore the present invention achieves rapid drug screening and will contribute to new drug development.

The invention claimed is:

1. A container for measuring cellular electric potential after being mounted on an electric potential measuring device, comprising a container and an electrode substrate, the electrode substrate being attached to a lower end of the container so as to form a plurality of wells, wherein the container comprises a plurality of cylindrical portions whose upper and lower ends are open, the electrode substrate comprises a substrate and a plurality of measurement electrodes and a plurality of reference electrodes disposed on one surface of the substrate, the measurement electrodes and the reference electrodes at least comprise metal-plated copper wiring on the substrate, a pair of a measurement electrode and a reference electrode are disposed on a bottom of each well, and the measurement electrodes and the reference electrodes, which are formed by a pre-plating method, further comprise a cured thermosetting resin paste printed on the metal-plated copper wiring of the substrate to suppress elution of copper from the measurement electrodes and the reference electrodes to a fluid accommodated in the wells weakening or killing cells to be measured.

2. A method for producing a container for measuring cellular electric potential after being mounted on an electric potential measuring device, wherein the container comprises a container and an electrode substrate, and the electrode substrate is attached to a lower end of the container so as to form a plurality of wells, the container comprises a plurality of cylindrical portions whose upper and lower ends are open, the electrode substrate comprises a substrate and a plurality of measurement electrodes and a plurality of reference electrodes disposed on one surface of the substrate, the measurement electrodes and the reference electrodes at least comprise metal-plated copper wiring on the substrate, a pair of a measurement electrode and a reference electrode are disposed on a bottom of each well, wherein the method comprises:

forming the measurement electrodes and the reference electrodes of the container by a pre-plating method, in which a thermosetting resin paste is printed on the substrate having a metal-plated copper wiring and the thermosetting resin is cured, to suppress elution of copper from the measurement electrodes and the reference electrodes to a fluid accommodated in the wells weakening or killing cells to be measured.

* * * * *